United States Patent
Ramakrishnan et al.

(10) Patent No.: US 7,431,951 B2
(45) Date of Patent: Oct. 7, 2008

(54) **ATHERMAL PROCESS FOR THE CONCENTRATION OF *GARCINIA* EXTRACT**

(75) Inventors: Chinnaswamy Anandha Ramakrishnan, Mysore (IN); Naveen Nagaraj, Mysore (IN); Guddadarangavvanahally Krishnareddy Jayaprakasha, Mysore (IN); Bhabani Sankar Jena, Mysore (IN); Mandyam Chakravarathy Varadaraj, Mysore (IN); Karumanchi Sreesaila Mallikarjuna Srinivasa Raghavarao, Mysore (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/509,831

(22) Filed: Aug. 24, 2006

(65) Prior Publication Data
US 2007/0154578 A1 Jul. 5, 2007

Related U.S. Application Data

(63) Continuation of application No. 10/743,278, filed on Dec. 22, 2003, now abandoned.

(51) Int. Cl.
 *A61K 36/00* (2006.01)
(52) U.S. Cl. .................................. 424/777; 424/725
(58) Field of Classification Search ................... None
See application file for complete search history.

(56) References Cited

U.S. PATENT DOCUMENTS 5,536,516 A 7/1996 Moffett et al.
5,972,357 A * 10/1999 Yamaguchi et al. ......... 424/401
6,299,777 B1 10/2001 Bowser

OTHER PUBLICATIONS

Jena, B.S., et al. "Organic Acids from Leaves, Fruits and Rinds of *Garcinia cowa*." J. Agri. Food Chem. (2002) 50(12), pp. 3431-3434.

* cited by examiner

*Primary Examiner*—Susan C Hoffman
(74) *Attorney, Agent, or Firm*—Ladas and Parry LLP

(57) ABSTRACT

The present invention relates to an athermal process of obtaining concentrated *Garcinia* extract by using osmotic membrane distillation (OMD).

10 Claims, No Drawings

ATHERMAL PROCESS FOR THE CONCENTRATION OF *GARCINIA* EXTRACT

This application is a continuation of application Ser. No. 10/743,278 filed on Dec. 22, 2003, now abandoned, claims the benefit thereof and incorporates the same by reference.

FIELD OF THE INVENTION

The present invention relates to an athermal process for the concentration of *Garcinia* extract. The present invention particularly relates to a process of obtaining concentrated *Garcinia* extract by using osmotic membrane distillation (OMD).

BACKGROUND OF THE INVENTION

As dietary supplement, (−)-Hydroxcitic acid (HCA) is an effective agent to any weight management program. Allison et al. (Crit. Rev. Food Sci. Nutr. 2001, 41, 1-28) has reviewed the use of HCA as one of the alternative treatments for weight loss. The derivatives of HCA have been incorporated into many pharmaceutical preparations in combination with other ingredients for the purpose of enhancing weight loss, cardio-protection, correcting the conditions of lipid abnormalities and endurance (Jena et al., 2002, J. Agric. Food Chemistry, 50, 10-22). So far HCA has been found in the fruits of certain species of *Garcinia*, which includes *G. cambogia, G. indica, G. atroviridis* and *G. cowa* (Lewis, Y. S. 1969, Methods in enzymology, 13, 613-623; Jena et al., 2002, J. Agric. Food Chemistry, 50, 10-22). The chemistry and biochemistry of HCA has been discussed recently (Jena et al., 2002, J. Agric. Food Chemistry, 50, 10-22). During extensive animal studies, HCA has been proven to effectively curb appetite, suppress food intake, increase the rates of hepatic glycogen synthesis, reduce fatty acid synthesis and lipogenesis and decrease body-weight gain. *Garcinia* (Family: Guttiferae) is a large genus of polygamous trees or shrubs, distributed in the tropical Asia, Africa and Polynesia. It consists of 180 species, out of which about 30 species are found in India. *G. pedunculata* and *G. cowa* are grown in Northeastern parts of India and Andaman Islands. In Assam *G. cowa* is often cultivated in homesteads for its acid fruits (The Wealth of India, 1956). The fruits from both the species of *Garcinia* are not palatable due to their strong acid taste. In Assam the sun dried slices of the fruits are used for culinary purposes and as folk medicine.

Reference may be made to the commercial samples of *Garcinia cambogia* extracts, where the HCA is present as its calcium salt (Sawada, et al, 1997, *Nihon yukagaka kaishi*, vol, 1467-1474). But the excess calcium reduces the solubility and subsequently bioavailability when it is compared to the liquid extract.

Another reference may be made to the Ashok kumar., Ravindranath, B., and Balasubramamanvam (U.S. Pat. No. 656,314, 1996). This process involves water extraction, followed by passing through ion exchange resins and decolorisation by using activated charcoal and finally concentration by using vacuum evaporation. The main drawback of this method is the thermal process and also it involves too many unit operations for obtaining the final product.

Reference may be made to Majeed et al. (Majeed, M., Badmaev, V and Rajendran, R. U.S. Pat. No. 5,783,603, 1998), wherein the preparation of potassium hydroxycitrate from *Garcinia* fruit was reported. It involves the extraction of *Garcinia* fruit using alkyl alcohol, the extract was treated with potassium hydroxide and refluxed to form potassium hydroxycitrate precipitate. The main drawback of this method is the potassium salt is hygroscopic. Further, HCA is not available in natural state, limiting its bioavailability and versatile applicability for pharmaceutical purposes.

It may be noted that all these references are mentioned above HCA derivatives preparations. But, there is no report on non-thermal process for concentrating of HCA and also in its native (not as derivatives) form.

OBJECTS OF THE INVENTION

The main object of the present invention is to develop a process for the concentrated *Garcinia* extract from *G. pedunculata/G. cowa* in liquid form.

Another object of present invention is to develop a non-thermal process for the concentration of *Garcinia* extract.

Still another object of the present invention is to develop a process for the concentrating of *Garcinia* extract using osmotic membrane distillation (OMD).

Yet another object of present invention is to provide a simple single step and efficient economical process for the concentration of HCA, where it is present in its native form.

DETAILED DESCRIPTION OF THE INVENTION

Accordingly, the present invention provides an athermal process for the concentrating of *Garcinia* extract, which comprises (a) collecting the dried fruit rinds may be effected from the species of *Garcinia*.
(b) cutting the rinds of *G. pedunculata/G. cowa* manually to a size of 3×9 mm to 6×14 mm.
(c) extracting may be effected with de-ionized water at a volume ratio of 1:4 for a period of 15-35 min at 110-130° C.
(d) filtering the above extract may be effected by filter cloth.
(e) concentrating the HCA by osmotic membrane distillation (OMD) in a co-current flat membrane module.
(f) placing a hydrophobic membrane between two steel frames SS316 of the module with suitable spaces.
(g) circulating the extract at a flow rate of 100-150 ml/min on the one side of the membrane using a multi-stage peristaltic pump.
(h) hydrophobic membrane osmotic agent (OA) on the other side of the membrane using a multi-stage peristaltic pump.
(i) carrying out OMD for about 4-6 hrs till the extract was concentrated in the feed tank.

In an embodiment of the present invention, the HCA concentration may be obtained from the aqueous extract of *G. pedunculata* and *G. cowa*.

In an another embodiment of the present invention, concentrated *Garcinia* extract may be obtained by using an athermal membrane process namely, Osmotic membrane distillation (OMD) at ambient temperature (25±1° C.) and pressure (1 atm).

Still another embodiment of present invention, the HCA content of the concentrated *Garcinia* extract is in the range of 33-37% estimated by HPLC method.

Yet in another embodiment of present invention the *Garcinia* extract was concentrated by a simple single step process where the HCA content was increased from 4-6 fold and HCA is present in the native form (not as derivative) with out formation of lactone, increasing it commercial and nutritive values.

In the present invention, rinds of *G. pedunculata/G. cowa* were cut into small pieces and extracted with de-ionized water. The above extract was filtered through filter cloth.

Concentrating the HCA by osmotic membrane distillation in a co-current flat membrane module. The membrane module consisted of two steel frames SS316 between which a hydrophobic membrane was placed. The entire filtrate was circulated on the one side of the OMD membrane and on the other side, an osmotic agent (OA) was circulated using a multi-stage peristaltic pump. After desired time the extract was concentrated in the feed tank.

The purity of the preparation was analyzed by HPLC as described by Jayaprakasha, G. K. and Sakariah, K. K. (J. Liquid Chromatography & Related Technologies, 23, 915-923, 2000). Concentrated hydroxycitric acid (0.1 g) was dissolved in water and made up to 100 ml with water and filtered. The high performance liquid chromatographic system consisted of a Hewlett Packard HPLC model HP 1100 Series (Hewlett-Packard, Calif., USA), fitted with a Waters μ-Bondapack™ (Waters Corporation, Milford, Mass., USA) $C_{18}$ column (250×4.6 mm I.D). The injection system (Rheodyne) used was 20 μl sample loop. Detection was done by a HP 1100 series variable wavelength detector at wavelength of 210 nm. The elution was carried out with 8 mM sulphuric acid and flow rate was 1.0 ml/min under isocratic condition. A known volume (10 μl) of the samples was injected on to the HPLC and the concentration of HCA was obtained directly from the peak area and by application of the dilution factor. The HCA concentration of the sample was expressed as g/100 g of sample. The purity of hydroxycitric acid was 33-35% (w/w).

The important aspects of the invention are:
1. Concentrated *Garcinia* extract is obtained by athermal membrane process.
2. This is a single step process for obtaining the concentrated *Garcinia* extract.
3. In the present process there is no phase change.
4. This process is operated at ambient temperature and pressure so that no thermal damage of the product.
5. HCA content was increased from 4-6 fold.
4. There is no lactone formation during this process.

The following examples are given by way of illustration of the present invention and should not be construed to limit the scope of the present invention.

EXAMPLE-1

Fruit rinds of *G. pedunculata* in 500 g quantity were cut into small pieces and extracted with 1.5 liters of de-ionized water for a period of 20 min at 120° C. The above extract was filtered through filter cloth. The extract was taken and subjected to concentration by osmotic membrane distillation in a co-current flat membrane module using micro porous hydrophobic polypropylene membrane of 0.05 μm at a flow rate of 100 ml/min. The module was operated in co-current mode using saturated calcium chloride as osmotic agent. The concentration was carried out till the volume of the extract was reduced to $\frac{1}{5}^{th}$ of the original volume. The concentration of HCA had increased from 6 to 62°Brix. The HCA content was determined by HPLC method and the acid was found to be 33.58% from an initial content of 5.09%. (6 fold enhancement).

EXAMPLE-2

Fruit rinds of *G. cowa* in 1000 g quantity were cut into small pieces and extracted with 3 liters of de-ionized water for a period of 30 min at 130 psi using autoclaving. The extract was filtered through filter cloth. The extract was taken and subjected to concentration by osmotic membrane distillation in a co-current flat membrane module using micro porous hydrophobic polypropylene membrane of 0.05 μm at a flow rate of 130 ml/min. The module was operated in co-current mode using saturated calcium chloride as osmotic agent. The concentration was carried out till the volume of the extract was reduced to $\frac{1}{5}^{th}$ of the original volume. The concentration of HCA had increased from 6 to 62°Brix. The HCA content was determined by HPLC method and the acid was found to be 35.5% from an initial content of 6%. (7 fold enhancement).

EXAMPLE-3

Fruit rinds of *G. pedunculata* in 100 μm quantity were cut into small pieces and extracting with 1 liter of de-ionized water for a period of 50 min at 120° C. using autoclaving. The extract was filtered through filter cloth. The extract was taken and subjected to concentration by osmotic membrane distillation in a co-current flat membrane module using micro porous hydrophobic polypropylene membrane of 0.05 μm at a flow rate of 150 ml/min. The module was operated in co-current mode using saturated calcium chloride as osmotic agent. The concentration was carried out till the volume of the extract was reduced to $\frac{1}{5}^{th}$ of the original volume. The concentration of HCA had increased from 6 to 62°Brix. The HCA content was determined by HPLC method and the acid was found to be 34.5% from an initial content of 5%. (6 fold enhancement).

The main advantages of the present invention are
1. This is a simple and single step process for obtaining the concentrated free HCA.
2. This concentrated *Garcinia* extract is in its native form without being any of its derivatives like sodium, potassium and calcium salts. Hence it will have better bioavailability.
3. This product does not undergo any thermal damage since the process is athermal, thereby the product is suitable for food/therapeutic applications.
4. This process is simpler and easy to scale-up.

We claim:
1. A process for concentrating an extract of one or more species of *Garcinia*, which comprises the steps of:
   a) extracting cut dried rinds of a fruit selected from *Garcinia pedunculata* and *G. cowa*, with de-ionized water at a volume ratio of 1:4 for a period of 20-30 minutes at 115° C.-130° C. to obtain an extract,
   b) filtering the extract to obtain a particle free extract, and
   c) subjecting the particle free extract to osmotic membrane distillation in a co-current mode in the presence of an osmotic agent to obtain a concentrated extract wherein the extract has been reduced to ⅕th of its original volume and obtaining (−)-hydroxycitric acid from the concentrated extract of step c).
2. The process as claimed in claim 1, wherein in step c) a hydrophobic membrane placed between two steel frames SS316 is used.
3. The process as claimed in claim 1 wherein the extract is circulated at a flow rate of 100-150 ml/minute on one side of the membrane using a multi-stage peristaltic pump.
4. The process as claimed in claim 3 wherein a hydrophobic membrane osmotic agent is placed on the other side of the membrane using a multi-stage peristaltic pump.
5. The process as claimed in claim 1 wherein the osmotic agent is saturated calcium chloride.
6. The process as claimed in claim 1 wherein the osmotic membrane distillation is carried out at ambient temperature of 25°+1° C. and pressure of 1 atm.

7. The process as claimed in claim 1 wherein the osmotic membrane distillation is carried on out for about 4-6 hrs. until the extract is concentrated.

8. The process as claimed in claim 1 wherein the (−)-hydroxycitric acid content in the concentrated extract is in the range 33-35% estimated by HPLC method.

9. The process as claimed in claim 1 wherein the (−)-hydroxycitric acid content in the concentrated extract is increased 4-6 fold as compared to the extract of step a) and the (−)-hydroxycitric acid is present in native form without formation of lactone.

10. A process for the concentration of *Garcinia* extract comprising the steps of:
   a) cutting dried rinds of *G. pedunculata, G. cowa* or a mixture thereof to a size of 3×9 mm to 6×14 mm;
   b) extracting the rinds using de-ionized water at a volume ratio of 1:4 for a period of 15-35 min at 110-130° C. to obtain an extract;
   c) filtering the extract using a filter cloth;
   d) concentrating (−)-hydroxycitric acid from the extract produced in step c) by osmotic membrane distillation (OMD) in a co-current flat membrane module wherein a hydrophobic membrane situated between two steel frames SS316 of the module with suitable spaces is used;
   e) circulating the extract at a flow rate of 100-150 ml/minute on one side of the membrane using a multi-stage peristaltic pump;
   f) using a hydrophobic membrane osmatic agent on the other side of the membrane using a multi-stage peristaltic pump; and
   g) carrying out OMD for about 4-6 hours until the extract is concentrated.

* * * * *